United States Patent [19]
Brooks

[11] Patent Number: 5,954,681
[45] Date of Patent: Sep. 21, 1999

[54] BREAST-SUPPORTING BAND

[76] Inventor: Diana Brooks, 1201 Newport, Hilton Head Island, S.C. 29928

[21] Appl. No.: 08/931,652

[22] Filed: Sep. 16, 1997

Related U.S. Application Data

[63] Continuation-in-part of application No. 08/785,692, Jan. 17, 1997, abandoned, which is a continuation-in-part of application No. 29/048,355, Dec. 27, 1995, abandoned.

[51] Int. Cl.[6] .................................. A61F 5/00; A41C 3/02
[52] U.S. Cl. ............................... 602/75; 602/19; 602/60; 602/79; 450/58
[58] Field of Search .......................... 602/79, 60; 450/65, 450/68, 69, 70, 2, 31, 34, 67, 74–76, 85; 2/67

[56] References Cited

U.S. PATENT DOCUMENTS

| | | |
|---|---|---|
| 56,592 | 11/1866 | Frieland . |
| 1,466,598 | 8/1923 | Panes . |
| 2,284,382 | 5/1942 | Elberfeld ........................................ 2/42 |
| 4,302,849 | 12/1981 | Margetson .................................... 2/115 |
| 4,816,005 | 3/1989 | Braaten ....................................... 450/58 |
| 4,909,771 | 3/1990 | Bergman ....................................... 450/3 |
| 5,011,452 | 4/1991 | Kelly .......................................... 450/69 |
| 5,499,965 | 3/1996 | Sanchea ...................................... 602/19 |
| 5,503,620 | 4/1996 | Danzar ........................................ 602/19 |
| 5,527,270 | 6/1996 | Chase et al. ................................ 602/41 |
| 5,538,502 | 7/1996 | Joahnstone ................................. 602/19 |
| 5,581,810 | 12/1996 | Yewer, Jr. ................................... 602/19 |
| 5,626,507 | 5/1997 | Gillen ......................................... 450/86 |

*Primary Examiner*—Michael A. Brown
*Assistant Examiner*—Kim M. Lee
*Attorney, Agent, or Firm*—Foley & Lardner

[57] ABSTRACT

A breast-supporting band is described to facilitate participation of women in sports with an elastic top edge, an elastic bottom edge, and an elastic middle band wider than the top and bottom edges having two side edges, in which the middle band stretches less than the top and bottom edges. The side edges of the middle band are fastened in front of a woman's chest.

18 Claims, 4 Drawing Sheets

BREAST-SUPPORTING BAND

This application is a continuation-in-part of Ser. No. 08/785,692, filed on Jan. 17, 1997 now abandoned, which is a continuation-in-part of design application Ser. No. 29/048,355, filed on Dec. 27, 1995 (now abandoned).

BACKGROUND OF THE INVENTION

Due to the high costs and side effects of breast reduction surgery, various attempts have been made to design athletic supporters for large-breasted women that facilitate their participation in sports. Although the prior art supporters offer some measure of increased support over regular bras, they are still insufficient for large breasted woman participating in active sports. These existing athletic support bras are primarily designed with individual cups supported by two shoulder straps which are affixed to a back panel. When the bra, and especially the straps, are designed to be stretchable there exists too much give in the material, creating a bouncing effect. Too little give in the material and an uncomfortable compressing effect occurs. There has yet to be developed a conventional athletic bra which is sufficiently resilient to provide comfort yet firm enough to provide adequate support for large breasted women. Even when the component parts of these bras are created larger or wider to provide better support, the shoulder straps still remain the basis of the supporting structure. This results in an uncomfortable strain on a relatively narrow area of the shoulder. Also, many of the prior art supporters require fastening at the sides or in back, creating difficulties in achieving a tight enough closure because of the awkward positioning.

For example, U.S. Pat. No. 4,957,466 discloses an athletic supporter for women comprising a front panel and a back panel with shoulder straps connecting the panels. The two panels fasten on either side by pinching together strips of hook and loop fasteners. The user must therefore reach to either side, while holding one arm up in the air, and pinch the two strips together using both hands. The awkward positioning of the fastening regions on the side makes it difficult to close off the panels and achieve a snug fit. Also, the multi-panel I design complicates manufacturing.

DETAILED DESCRIPTION OF THE INVENTION

The present invention relates to a breast-supporting band to facilitate participation of women, especially large-breasted women, in sports comprising a substantially rectangular elastic panel with a top edge, a bottom edge, and two side edges, said elastic panel having (1) a middle band attached around an outer middle section of the panel extending between the two side edges leaving exposed top and bottom edges of the elastic panel (as in FIGS. 1 and 2) or (2) wherein the top edge, the bottom edge and the middle band are three separate pieces of material attached to each other (as in FIGS. 3 and 4), said middle band being wider than the top and bottom edges of the elastic panel, and means for fastening the two side edges of the elastic panel together. Depending on the size of the user, the size of the panel is adjusted appropriately, but should be of a size sufficient to substantially flatten and immobilize a user's breasts when fastened around the chest, so that the flattened breasts are completely covered by the material of the band. Preferably, the band is large enough to reach from a position just underneath the arm to a position around the bottom of the rib cage.

Means for fastening the two edges together include VEL-CRO™ (hook and loop material) and metal hooks that fit into rings or loops sewed into a strip of fabric. Multiple rows of rings may be used to adjust for different sizes.

The top and bottom edges of the elastic panel are preferably made of an elastic material that stretches more than the middle band. An elastic material suitable for the top and bottom edges is the elastic used in waistbands. Preferably, the elastic material of the top and bottom edges stretches in a longitudinal direction, but does not substantially stretch widthwise. This helps prevent downward or upward slippage of the breast-supporting band.

The middle band of material (attached around the middle section of the elastic panel or which is attached to the top and bottom edges as three separate pieces) is wider than the top and bottom edges and made of a stretchable material that does not stretch as much as the elastic top and bottom edges. Greater give in the top and bottom edges helps prevent pinching caused by skin overhang. Preferably, the middle band is made of a material that stretches in any direction. A preferred material for the middle band that stretches in any direction is LYCRA™ (stretch-woven fabric). Stretching in any direction allows the middle band to flatten and immobilize the breasts uniformly across the chest without forcing them in any one direction.

Figure 1:
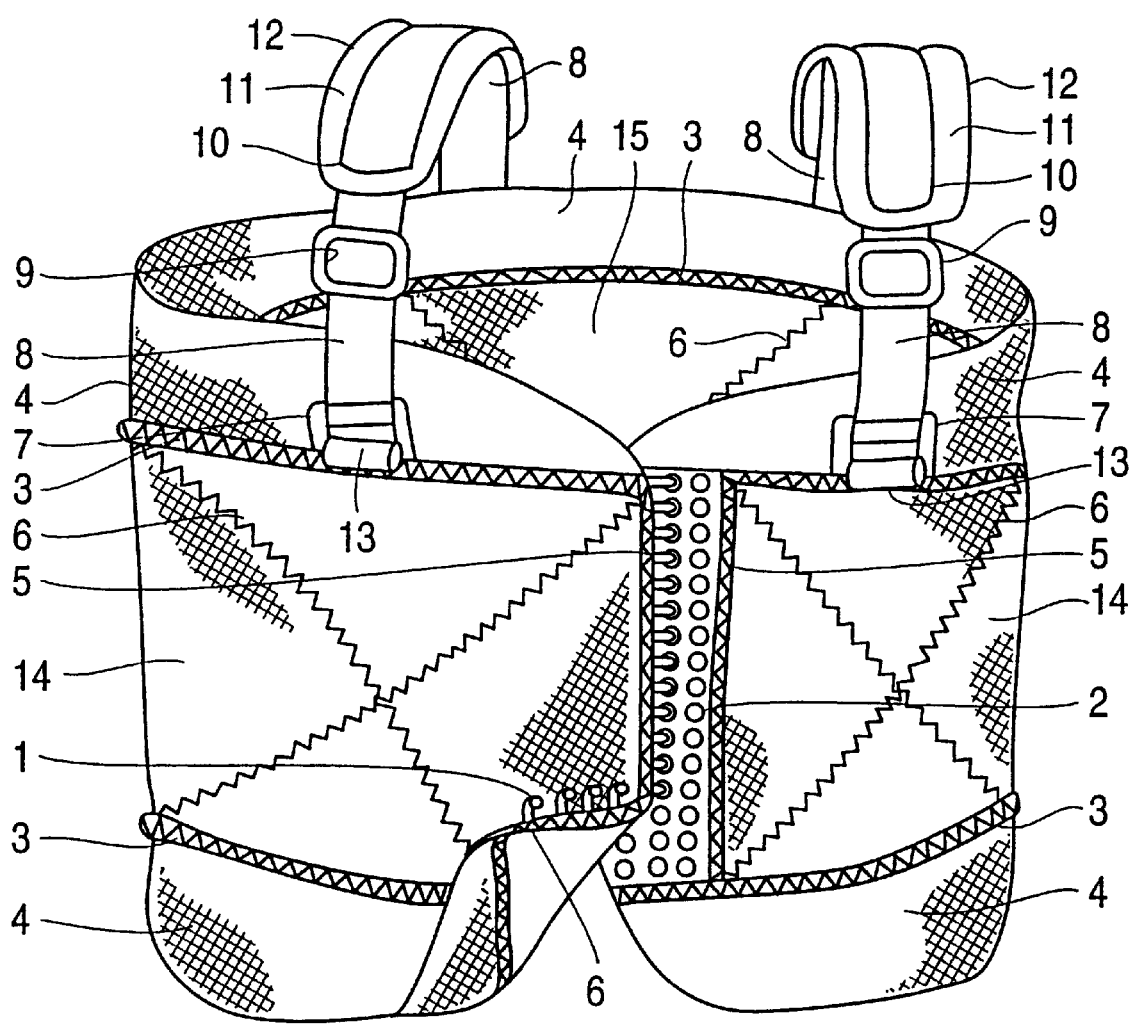
FIG. 1 is a front view of a breast-supporting band according to the present invention.

Referring to FIG. 1, the breast-supporting band includes a single row of hooks 1 along one side edge of the elastic panel 4 which attaches into the rows of loops 2 on the other side edge of the panel 14. Stitching along side edges 5 secures the hooks 1 and loops 2 in place along the side edges 5. Exposed regions of the elastic panel 4 along the top and bottom edges prevent upward and downward slippage. A middle support band of material 14 is stitched along lines 6 for attachment to the outer surface of the elastic panel 4. Optional shoulder straps 8 attach by means of detachable clips 7 through loops 13 fastened to panel 4 along stitching line 3. Buckles 9 allow adjustment of the size of shoulder straps 8. Optional shoulder pads 11 with zigzag edge stitching 12 attach to shoulder straps 8 through slots 10. On the inside of the panel 4, an optional middle band of absorbent material 15 is sewed in place along stitching lines 6 to soak up perspiration during physical exercise.

Figure 2:
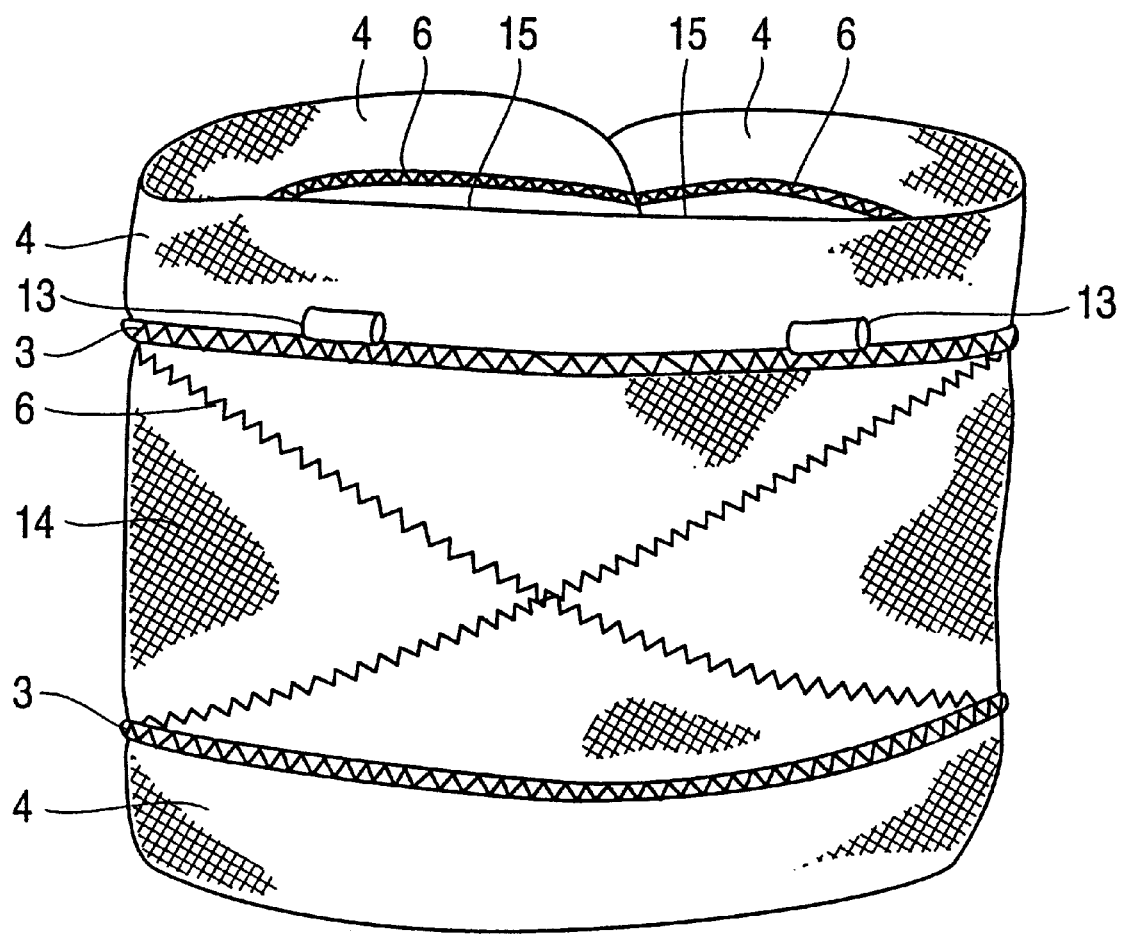
FIG. 2 is a rear view of the breast-supporting band of FIG. 1 with the optional shoulder straps removed.

FIG. 2 shows a rear view of the embodiment of FIG. 1 without shoulder straps. The outer band 14 reaches all the way around the elastic panel 4 and is attached along stitching lines 3 and 6. The inner absorbent band 15 is seen partially along the inner surface of elastic panel 4. Also shown are the rear attachment loops 13 for the optional shoulder straps (not shown).

In use, the breast-supporting band is fastened around the chest and attached in front, where the user's hands can easily fasten the side edges of the elastic panel together. The breast-supporting band of the present invention is advantageous because of its ease of construction, ease of fastening, and substantial immobilization of the breasts to facilitate participation in sports, especially sports such as golf where the arms must pass in front of the chest during the swing of the club.

The breast-supporting band of FIGS. 1 and 2 is easily constructed by making two single-cut rectangular elastic pieces, attaching the smaller one to the outside of the larger one, and attaching fastening means thereto.

Figure 3:
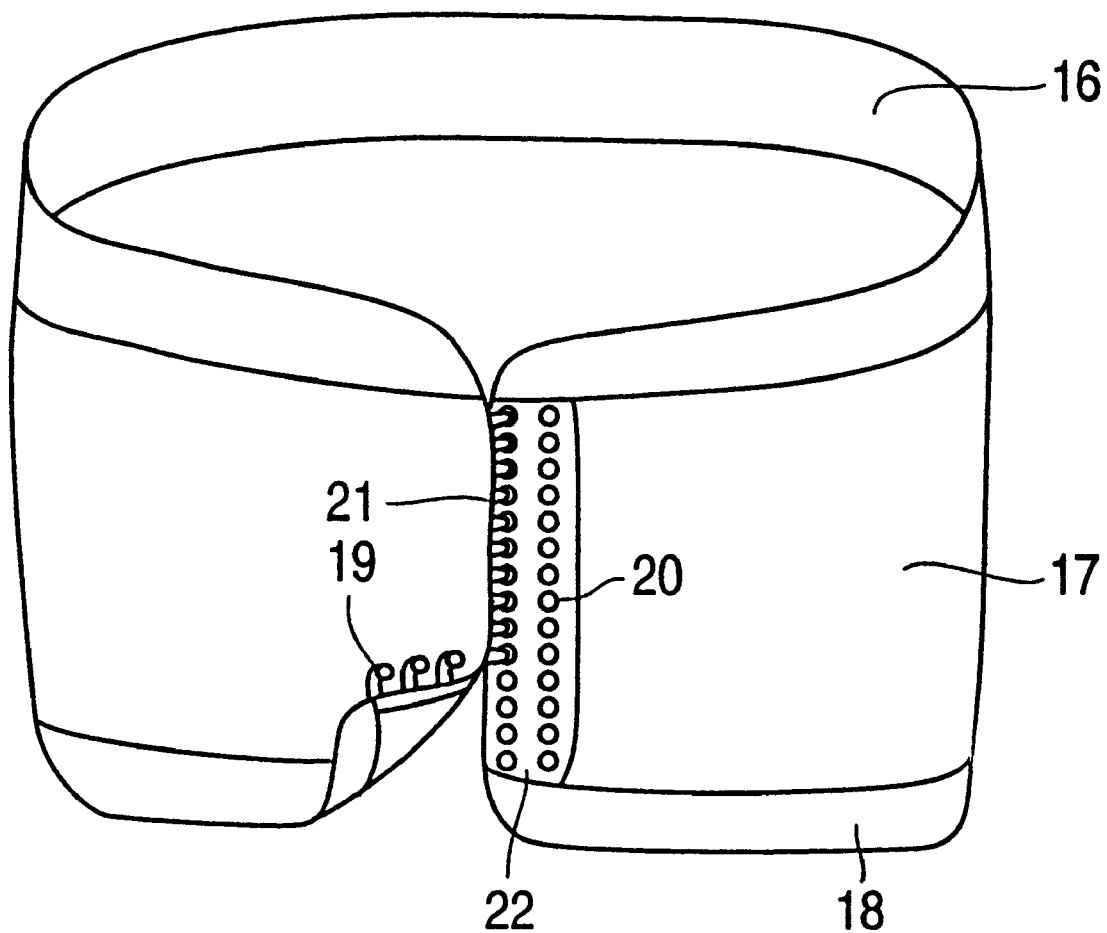
FIG. 3 is a front view of an alternative embodiment utilizing a three-piece construction of materials.
Figure 4:
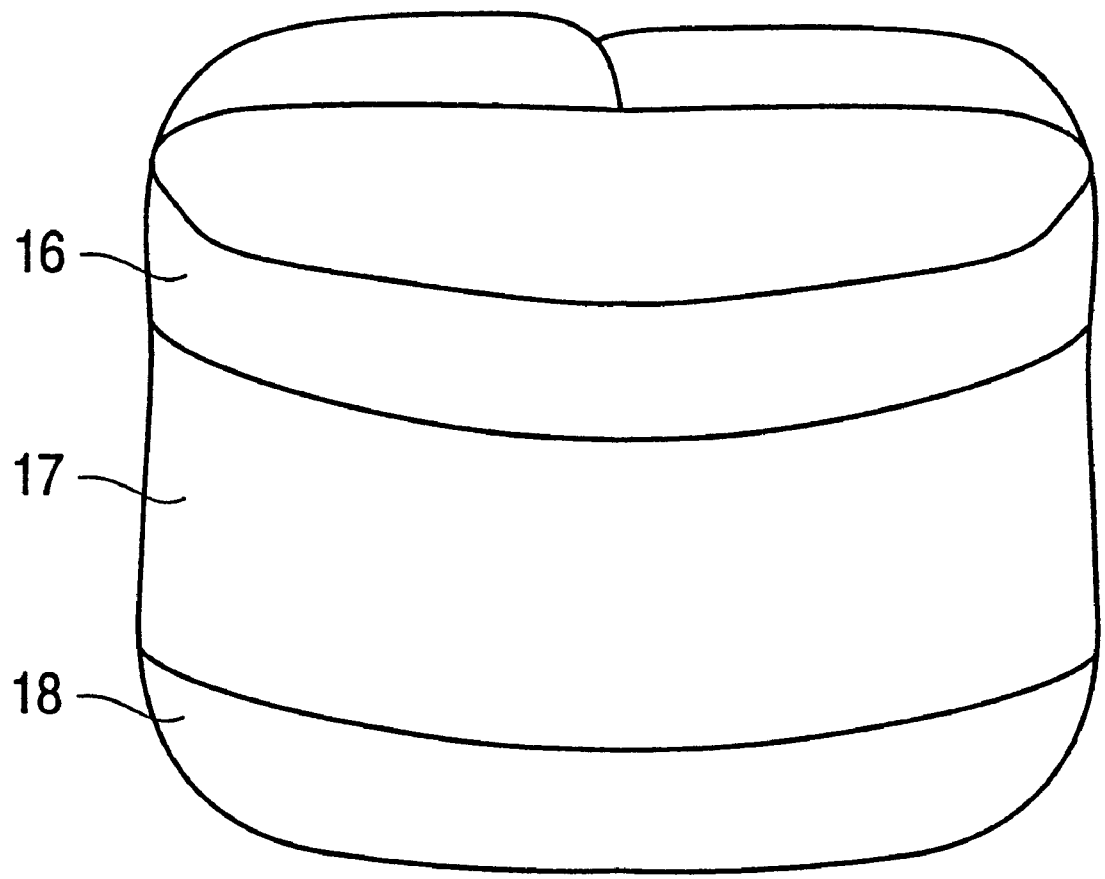
FIG. 4 is a rear view of an alternative embodiment utilizing a three-piece construction of materials.

FIGS. 3 and 4 show front and rear views, respectively, of an alternative embodiment of the present invention in which top edge 16, middle band 17, and bottom edge 18 are three separate pieces, preferably joined together by stitching. Top edge 16 and bottom edge 18 are preferably elastic, and more preferably, an elastic which stretches longitudinally but not widthwise (up and down). Middle band 17, which is wider than both top edge 16 and bottom edge 18, is made of a material that stretches less in any direction than top edge 16 and bottom edge 18 stretch in a longitudinal direction. The higher elasticity of the top edge 16 and bottom edge 18 helps prevent pinching otherwise caused when skin underneath the arm overhangs the top edge 16. Preferably, the material of middle band 17 is a material that stretches in any direction to permit flattening of the breasts in the direction of least resistance, for example LYCRA™ (stretch-woven fabric), provided that the material stretches less in any direction than the top edge 16 and bottom edge 18 stretch in a longitudinal direction. Also, the middle band preferably has a substantially rectangular, flat shape with no cups. In a still more preferred embodiment, the top edge 16 and bottom edge 18 are sewed over the outer side of the middle band 17, so that the middle band underlies the top edge 16 and bottom edge 18; for this embodiment, the middle band 17 is bunched together along the top and lower edges of the top edge 16 and bottom edge 18, respectively, to permit the greater elasticity of the top edge 16 and bottom edge 18 to stretch their full length. The breast-supporting band of FIGS. 3 and 4 also preferably includes a single row of hooks 19 along one side edge 21 of the middle band 17 which attaches into the rows of loops 20 on the other side edge 22 of the middle band 17. Preferably, stitching along side edges 21 and 22 secures the hooks 19 and loops 20 in place along the side edges 21 and 22.

It will be apparent to those skilled in the art that various modifications and variations can be made to the compositions and processes of this invention. Thus, it is intended that the present invention cover such modifications and variations, provided they come within the scope of the appended claims and their equivalents.

The disclosures of all publications cited above are expressly incorporated herein by reference in their entireties to the same extent as if each were incorporated by reference individually.

I claim:

1. A breast-supporting band to facilitate participation of women in sports comprising an elastic top edge, an elastic bottom edge, an elastic middle band wider than both the top and bottom edges having two side edges, and means for fastening the two side edges of the middle band together in front of a woman's chest, said elastic middle band being made of a material that stretches less than the elastic top and bottom edges, whereby a woman's breasts are substantially flattened and immobilized when the side edges are fastened together.

2. The breast-supporting band of claim 1, wherein the means for fastening the two side edges together comprises a plurality of hooks on one side edge that attach to a plurality of rings on the other side edge.

3. The breast-supporting band of claim 2, wherein multiple rows of rings are arranged vertically to adjust for different sizes.

4. The breast-supporting band of claim 1, further comprising an inner middle band of absorbent material.

5. The breast-supporting band of claim 1, further comprising detachable shoulder straps.

6. The breast-supporting band of claim 5, wherein the shoulder straps include shoulder pads.

7. The breast-supporting band of claim 1, wherein the middle band is substantially rectangular.

8. The breast-supporting band of claim 7, wherein the top and bottom edges stretch longitudinally but substantially do not stretch up or down to prevent upward or downward slippage when worn around a woman's chest.

9. The breast-supporting band of claim 8, wherein the middle band stretches in any direction to permit flattening of the breasts in a direction of least resistance but which stretches less in any direction than the top and bottom edges stretch in a longitudinal direction.

10. A method of supporting a woman's breasts during sports or exercise comprising fastening in front of the woman's chest two side edges of a breast-supporting band comprising an elastic top edge, an elastic bottom edge, an elastic middle band wider than both the top and bottom edges having the two side edges, said elastic middle band being made of a material that stretches less than the elastic top and bottom edges, whereby the woman's breasts are substantially flattened and immobilized when the side edges are fastened together.

11. The method of claim 10, wherein the breast-supporting band includes a plurality of hooks on one side edge that attach to a plurality of rings on the other side edge.

12. The method of claim 11, wherein multiple rows of rings are arranged vertically to adjust for different sizes.

13. The method of claim 10, wherein the breast-supporting band further comprises an inner middle band of absorbent material.

14. The method of claim 10, wherein the breast-supporting band further comprises detachable shoulder straps.

15. The method of claim 14, wherein the shoulder straps include shoulder pads.

16. The method of claim 10, wherein the middle band is substantially rectangular.

17. The method of claim 16, wherein the top and bottom edges stretch longitudinally but substantially do not stretch up or down to prevent upward or downward slippage.

18. The method of claim 17, wherein the middle band stretches in any direction to permit flattening of the breasts in a direction of least resistance but which stretches less in any direction than the top and bottom edges stretch in a longitudinal direction.

\* \* \* \* \*